(12) United States Patent
Hu et al.

(10) Patent No.: US 11,707,235 B2
(45) Date of Patent: Jul. 25, 2023

(54) SYSTEMS AND METHODS FOR CONTROLLING IMAGING

(71) Applicant: SHANGHAI UNITED IMAGING HEALTHCARE CO., LTD., Shanghai (CN)

(72) Inventors: Lingzhi Hu, Houston, TX (US); Xinyuan Xia, Shanghai (CN); Jiaxu Zheng, Shanghai (CN); Yuhang Shi, Shanghai (CN); Tuoyu Cao, Houston, TX (US); Hui Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 1060 days.

(21) Appl. No.: 16/455,869

(22) Filed: Jun. 28, 2019

(65) Prior Publication Data
US 2020/0352524 A1    Nov. 12, 2020

(30) Foreign Application Priority Data
May 8, 2019 (CN) .......................... 201910378793.3

(51) Int. Cl.
*A61B 5/00* (2006.01)
*G01R 33/54* (2006.01)
(Continued)

(52) U.S. Cl.
CPC .......... *A61B 5/7292* (2013.01); *G01R 33/543* (2013.01); *G01R 33/56509* (2013.01);
(Continued)

(58) Field of Classification Search
CPC combination set(s) only.
See application file for complete search history.

(56) References Cited

U.S. PATENT DOCUMENTS

2004/0010210 A1    1/2004  Avinash et al.
2009/0192384 A1*   7/2009  Fontius .................. A61B 6/527
                                                        600/425
(Continued)

FOREIGN PATENT DOCUMENTS

CN      103892613 A    7/2014
CN      104569963 A    4/2015
(Continued)

OTHER PUBLICATIONS

F. Thiel et al., Combining Magnetic Resonance Imaging and Ultrawideband Radar: A New Concept for Multimodal Biomedical Imaging, Review of Scientific Instruments, 80:014302-1 to 014302-10, 2009.
(Continued)

*Primary Examiner* — Joel F Brutus
(74) *Attorney, Agent, or Firm* — Metis IP LLC

(57) ABSTRACT

A method for controlling a medical device may be provided. The method may include obtaining, via one or more cameras, first data regarding a first motion of a subject in an examination space of the medical device. The method may include obtaining, via one or more radars, second data regarding a second motion of the subject. The method may further include generating, based on the first data and the second data, a control signal for controlling the medical device to scan at least a part of the subject.

20 Claims, 13 Drawing Sheets

(51) Int. Cl.
  *G01R 33/565* (2006.01)
  *G01S 13/50* (2006.01)
  *G01S 13/86* (2006.01)
  *G06T 7/20* (2017.01)
  *G06T 11/00* (2006.01)

(52) U.S. Cl.
  CPC ............ *G01S 13/50* (2013.01); *G01S 13/867* (2013.01); *G06T 7/20* (2013.01); *G06T 11/008* (2013.01); *G06T 2207/10081* (2013.01); *G06T 2207/10088* (2013.01); *G06T 2207/10104* (2013.01); *G06T 2207/10132* (2013.01); *G06T 2207/20201* (2013.01); *G06T 2207/30048* (2013.01); *G06T 2210/41* (2013.01); *G06T 2211/404* (2013.01)

(56) References Cited

U.S. PATENT DOCUMENTS

| | | |
|---|---|---|
| 2009/0245457 A1 | 10/2009 | Takeuchi et al. |
| 2010/0290683 A1 | 11/2010 | Demeester et al. |
| 2012/0169333 A1 | 7/2012 | Katscher et al. |
| 2013/0251225 A1 | 9/2013 | Liu et al. |
| 2015/0002331 A1 | 1/2015 | Allmendinger et al. |
| 2015/0366527 A1* | 12/2015 | Yu .......................... A61B 6/527 600/407 |
| 2017/0016972 A1 | 1/2017 | Bhat et al. |
| 2017/0206668 A1 | 7/2017 | Poulos et al. |
| 2018/0098739 A1 | 4/2018 | Freeman et al. |
| 2018/0368721 A1 | 12/2018 | Ahn |
| 2021/0059628 A1 | 3/2021 | Yang et al. |

FOREIGN PATENT DOCUMENTS

| | | |
|---|---|---|
| CN | 103315739 B | 8/2015 |
| CN | 103584919 B | 1/2016 |
| CN | 106251380 A | 12/2016 |
| CN | 109199346 A | 1/2019 |
| CN | 109363702 A | 2/2019 |
| JP | 5942244 B2 | 6/2016 |
| WO | 2010069168 A1 | 6/2010 |

OTHER PUBLICATIONS

Stefano Pisa et al., A Survey of Radar Systems for Medical Applications, IEEE A&E Systems Magazine, 64-81, 2016.
F.Thiel et al., Non-contact Detection of Myocardium's Mechanical Activity by Ultrawideband RF-radar and Interpretation Applying Electrocardiography, Review of Scientific Instruments, 80: 114302-1 to 114302-12, 2009.

* cited by examiner

SYSTEMS AND METHODS FOR CONTROLLING IMAGING

CROSS-REFERENCE OF RELATED APPLICATION

This application claims priority of Chinese Patent Application No. 201910378793.3, filed on May 8, 2019, the contents of which are hereby incorporated by reference.

TECHNICAL FIELD

The present disclosure generally relates to a medical device, and more particularly, relates to systems and methods for controlling imaging of the medical device.

BACKGROUND

Imaging is widely used in a variety of medical treatments and/or diagnostics. Various imaging devices (e.g., a computed tomography (CT) device, a magnetic resonance imaging (MRI) device, or a positron emission tomography (PET) device) can be used to perform imaging by scanning a subject (e.g., a patient). A motion of the subject during the scan, such as a cardiac motion or a respiratory motion, may cause motion artifacts. For example, during an MRI scan, if the patient moves his or her head, a final reconstructed image may include motion artifacts and/or become blurry. In this case, a diagnosis and treatment of a disease on the basis of the reconstructed image including the motion artifacts may be unreliable due to a poor image quality. Therefore, it is desirable to develop systems or methods to control an imaging device in order to reduce or avoid motion artifacts in imaging.

SUMMARY

According to a first aspect of the present disclosure, a method for controlling a medical device is provided. The method may include may include one or more operations. The one or more operations may be implemented by at least one processing device. The at least one processing device may obtain, via one or more cameras, first data regarding a first motion of a subject in an examination space of the medical device. The at least one processing device may obtain, via one or more radars, second data regarding a second motion of the subject. The at least one processing device may generate, based on the first data and the second data, a control signal for controlling the medical device to scan at least a part of the subject.

In some embodiments, the at least one processing device may obtain scan data acquired by the medical device, and reconstruct a medical image based on the scan data.

In some embodiments, the at least one processing device may acquire, via the one or more cameras, a plurality of image frames regarding the first motion of the subject. The at least one processing device may determine, based on at least a part of the plurality of image frames, the first data including one or more motion parameters of the first motion.

In some embodiments, the one or more motion parameters of the first motion may include one or more translation matrices and one or more rotation matrices.

In some embodiments, the at least one processing device may acquire, via the one or more radars, radar echo data from the subject. The at least one processing device may correct the radar echo data according to the one or more motion parameters of the first motion, and extract, from the corrected radar echo data, the second data including cardiac motion data or respiratory motion data.

In some embodiments, the plurality of image frames and the radar echo data may be acquired simultaneously by the one or more cameras and the one or more radars, respectively.

In some embodiments, the at least one processing device may generate, based at least in part on the second data, the control signal using a gating technique.

In some embodiments, the first motion may include a rigid motion of the subject, and the second motion may include a physiological motion of the subject.

In some embodiments, the medical device may include at least one of a computed tomography (CT) device, a magnetic resonance imaging (MRI) device, a positron emission tomography (PET) device, or a radiation therapy (RT) device.

According to a second aspect of the present disclosure, a system for controlling a medical device may be provided. The system may include at least one storage device including a set of instructions, and at least one processor in communication with the at least one storage device. When executing the set of instructions, the at least one processor may obtain, via one or more cameras, first data regarding a first motion of a subject in an examination space of the medical device. The at least one processor may obtain, via one or more radars, second data regarding a second motion of the subject. The at least one processor may generate, based on the first data and the second data, a control signal for controlling the medical device to scan at least a part of the subject.

According to a third aspect of the present disclosure, a medical system may be provided. The medical system may include a medical device, one or more cameras, one or more radars, at least one storage device including a set of instructions, and at least one processor in communication with the at least one storage device. The one or more cameras may be configured to acquire a plurality of image frames of a subject in an examination space of the medical device. The one or more radars may be configured to acquire radar echo data from the subject. When executing the set of instructions stored in at least one storage device, the at least one processor is directed to cause the medical system to determine, based on the plurality of image frames, first data regarding a first motion of the subject. The at least one processor is directed to cause the medical system to determine, based on the radar echo data, second data regarding a second motion of the subject. The at least one processor is directed to cause the medical system to generate, based on the first data and the second data, a control signal for controlling the medical device to scan at least a part of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
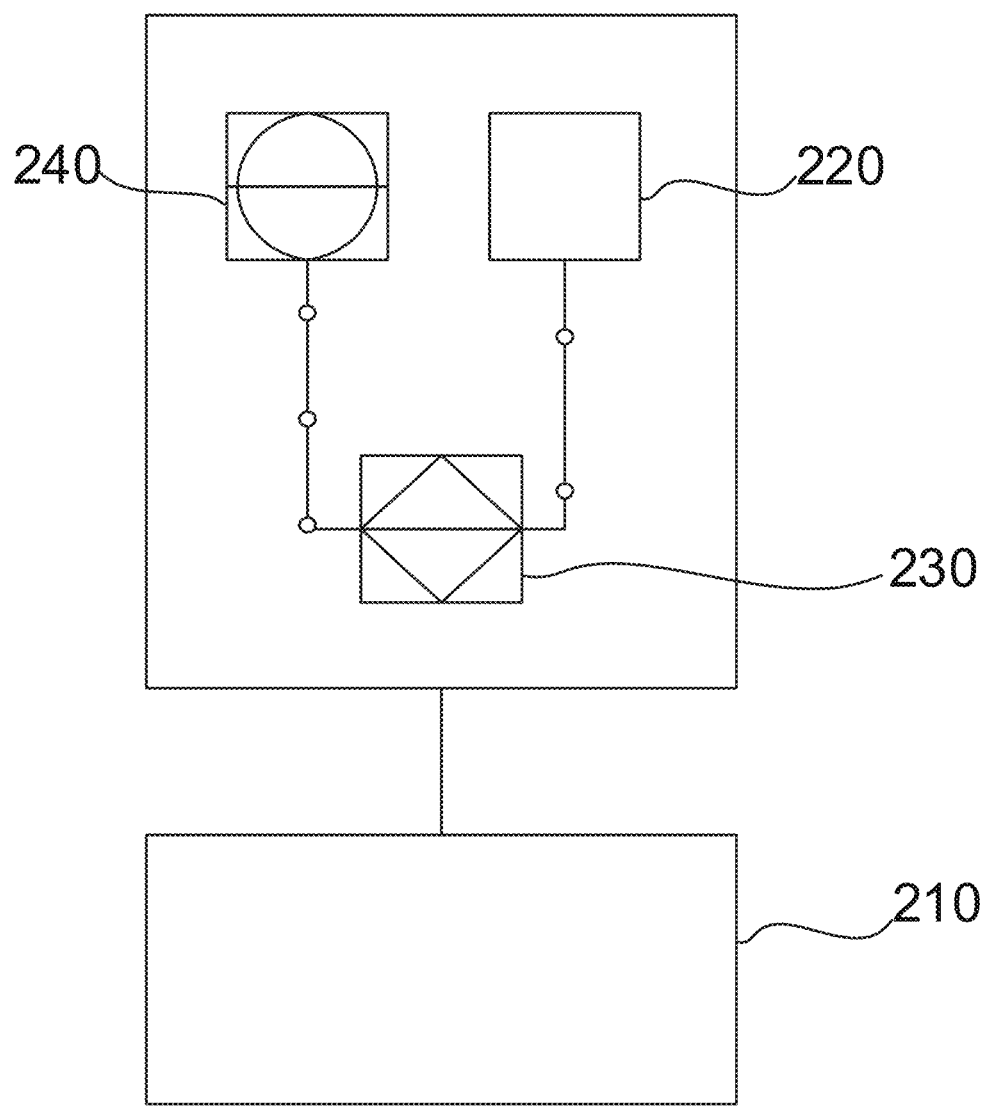
FIG. 2 is a schematic diagram illustrating an exemplary medical device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processing device 240 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Provided herein are systems and components for medical imaging and/or medical treatment. In some embodiments, the medical system may include one or more modalities including Digital Subtraction Angiography (DSA), Magnetic Resonance Imaging (MRI), Magnetic Resonance Angiography (MRA), Computed tomography (CT), Computed Tomography Angiography (CTA), Ultrasound Scanning (US), Positron Emission Tomography (PET), Single-Photon Emission Computerized Tomography (SPECT), CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, Vide-US, or the like, or any combination thereof.

An aspect of the present disclosure relates to systems and methods for controlling a medical device. The medical device may include a medical imaging device, e.g., an MRI device. In some embodiments, the system may include one or more radars, and one or more cameras. The medical device may be controlled by fusing data acquired by the one or more radars and the one or more cameras. For example, the system may determine first data regarding a first motion of a subject by processing a plurality of image frames acquired by the one or more cameras. The system may determine second data regarding second data regarding a second motion of the subject by processing radar echo data acquired by the one or more radars. The radar echo data may be corrected based on the first data. In some embodiments, the first motion may include a rigid motion of the subject, and the second motion may include a physiological motion. The system may extract physiological motion information based on the first data and the second data. For example, the physiological motion information may include cardiac motion data and/or respiratory motion data. The system may control, based on the physiological motion information, the medical device in order to reduce or avoid the effect of motion artifacts in, e.g., imaging, delivery of a treatment dosage (e.g., a radiation beam toward a target region).

The following description is provided with reference to exemplary embodiments that the medical device include an imaging device (e.g., a scanner) unless otherwise stated. However, it is understood that it is for illustration purposes only and not intended to limit the scope of the present disclosure. The system and method disclosed herein may be suitable for other applications. Merely by way of example, the medical device may include a radiotherapy device (an image-guided radiotherapy (IGRT) device); the system and method for identifying a physiological motion may be used in controlling the delivery of a radiation beam in radiotherapy.

Figure 1:
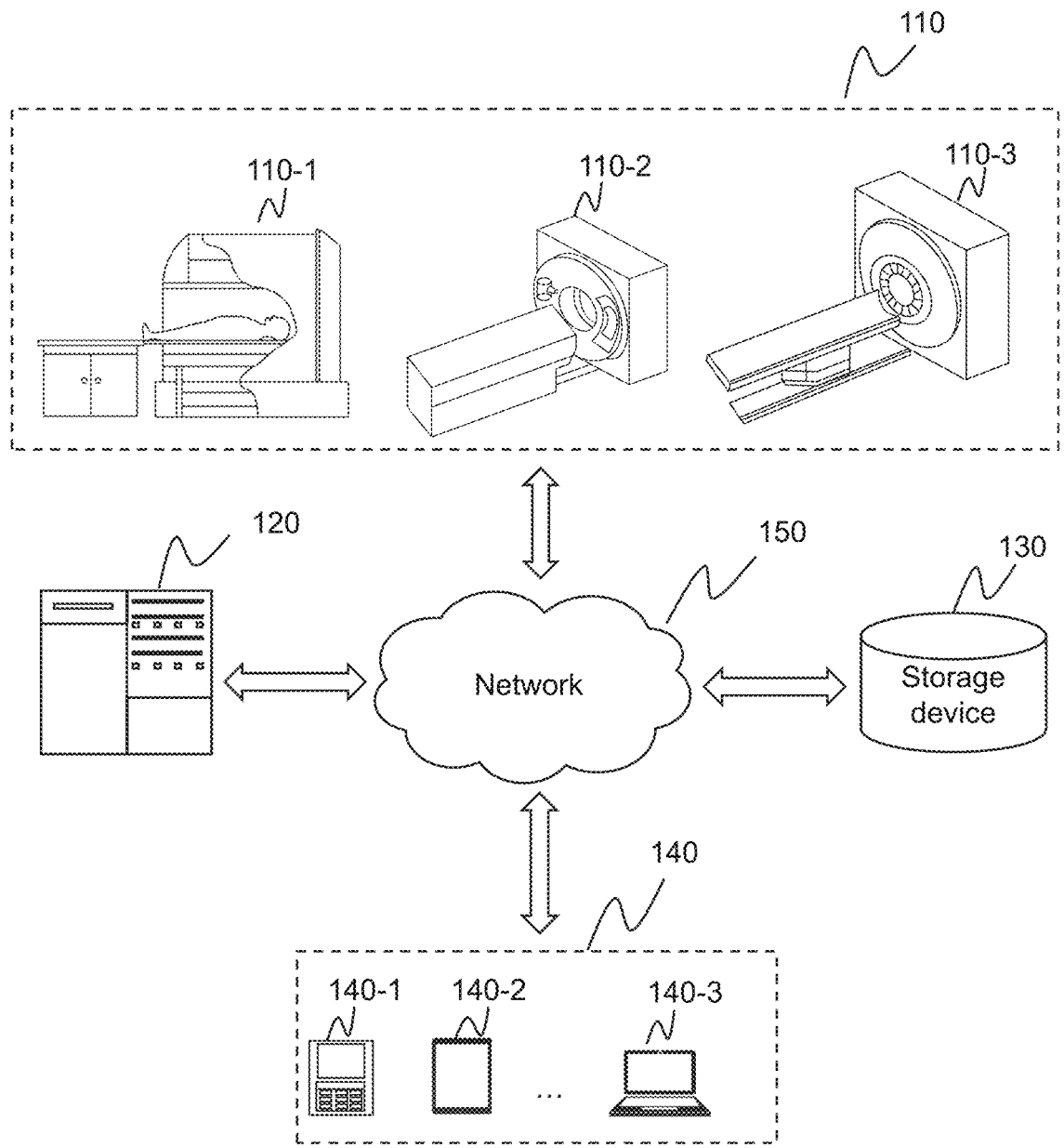
FIG. 1 is a schematic diagram illustrating an exemplary medical system according to some embodiments of the present disclosure.

FIG. 1 is a schematic diagram illustrating an exemplary medical system according to some embodiments of the present disclosure. As shown in FIG. 1, medical system 100 may include a medical device 110, a processing device 120, a storage device 130, one or more terminals 140, and a network 150. The components in the medical system 100 may be connected in one or more of various ways. Merely by way of example, as illustrated in FIG. 1, the medical device 110 may be connected to the processing device 120 through the network 150. As another example, the medical device 110 may be connected to the processing device 120 directly as indicated by the bi-directional arrow in dotted lines linking the medical device 110 and the processing device 120. As a further example, the storage device 130 may be connected to the processing device 120 directly or through the network 150. As still a further example, one or more terminals 140 may be connected to the processing device 120 directly (as indicated by the bi-directional arrow in dotted lines linking the terminal 140 and the processing device 120) or through the network 150.

The medical device 110 may generate or provide image data by scanning a subject or at least a part of the subject. In some embodiments, the medical device 110 may be a medical imaging device, for example, a positron emission tomography (PET) device, a single photon emission computed tomography (SPECT) device, a computed tomography (CT) device, a magnetic resonance imaging (MRI) device, a radiation therapy (RT) device, or the like, or any combination thereof. In some embodiments, the medical device 110 may include a single-modality scanner. The single-modality scanner may include, for example, a magnetic resonance imaging (MRI) scanner 110-1, a computed tomography (CT) scanner 110-2, and/or a positron emission tomography (PET) scanner 110-3. In some embodiments, the medical device 110 may include both the CT scanner 110-2 and the PET scanner 110-3. In some embodiments, image data of different modalities related to the subject, such as CT image data and PET image data, may be acquired using different scanners separately. In some embodiments, the medical device 110 may include a multi-modality scanner. The multi-modality scanner may include a positron emission tomography-computed tomography (PET-CT) scanner, a positron emission tomography-magnetic resonance imaging (PET-MRI) scanner, or the like, or any combination thereof. The multi-modality scanner may perform multi-modality imaging simultaneously. For example, the PET-CT scanner may generate structural X-ray CT image data and functional PET image data simultaneously in a single scan. The PET-MRI scanner may generate MRI data and PET data simultaneously in a single scan. In some embodiments, the medical device 110 may include an image-guided radiotherapy (IGRT) device (not shown in FIG. 1). For example, the IGRT device may include a positron emission tomography-radiotherapy (PET-RT) device, or a magnetic resonance imaging-radiotherapy (MRI-RT) device, etc.

In some embodiments, the subject may include a body, a substance, or the like, or any combination thereof. In some embodiments, the subject may include a specific portion of a body, such as a head, a thorax, an abdomen, or the like, or any combination thereof. In some embodiments, the subject may include a specific organ, such as an esophagus, a trachea, a bronchus, a stomach, a gallbladder, a small intestine, a colon, a bladder, a ureter, a uterus, a fallopian tube, etc. In some embodiments, the subject may include a physical model (e.g., a water phantom). In the present disclosure, "object" and "subject" are used interchangeably. In some embodiments, the medical device 110 may include a scanning table. The subject may be placed on the scanning table for imaging.

In some embodiments, the medical device 110 may transmit the image data via the network 150 to the processing device 120, the storage device 130, and/or the terminal(s) 140. For example, the image data may be sent to the processing device 120 for further processing, or may be stored in the storage device 130. In some embodiments, the medical device 110 may be configured to scan the subject or at least a part of the subject in response to a control signal generated by the processing device 120.

The processing device 120 may process data and/or information obtained from the medical device 110, the storage device 130, and/or the terminal(s) 140. For example, the processing device 120 may obtain first data regarding a first motion of the subject through one or more cameras disposed in the medical device 110. The processing device 120 may obtain second data regarding a second motion of the subject through one or more radars disposed in the medical device 110. The processing device 120 may generate a control signal based on the first data and the second data. As another example, the processing device 120 may generate an image (e.g., an MR image) by reconstructing scan data acquired by the medical device 110 (e.g., an MRI device).

In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the terminal(s) 140 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage device 130 may store data, instructions, and/or any other information. In some embodiments, the storage device 130 may store data obtained from the medical device 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140, etc.). One or more components in the medical system 100 may access the data or instructions stored in the storage device 130 via the network 150. In some embodiments, the storage device 130 may be part of the processing device 120.

The terminal(s) 140 may be connected to and/or communicate with the medical device 110, the processing device 120, and/or the storage device 130. For example, the terminal(s) 140 may obtain a processed image from the processing device 120. As another example, the terminal(s) 140 may obtain scan data acquired by the medical device 110 and transmit the scan data to the processing device 120 to be processed. In some embodiments, the terminal(s) 140 may include a mobile device 140-1, a tablet computer 140-2, a laptop computer 140-3, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate exchange of information and/or data for the medical system 100. In some embodiments, one or more components of the medical system 100 (e.g., the medical device 110, the processing device 120, the storage device 130, the terminal(s) 140, etc.) may communicate information and/or data with one or more other components of the medical system 100 via the network 150. For example, the processing device 120 may obtain image data from the medical device 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 130 may be a data storage including cloud computing platforms, such as, a public cloud, a private cloud, a community cloud, and a hybrid cloud, etc. However, those variations and modifications do not depart from the scope of the present disclosure.

FIG. 2 is a schematic diagram illustrating an exemplary medical device according to some embodiments of the present disclosure. As shown in FIG. 2, medical device 220 may include a scanner 210, one or more radars 220, one or more cameras 230, and a processing device 240. The scanner 210 may be configured to scan a subject or at least a part of the subject, and acquire corresponding scan data. The one or more radars 220 may be configured to acquire radar echo data from the subject. In some embodiments, the radar echo data may include data related to a physiological motion of the subject (hereinafter physiological motion related data). In some embodiments, the radar echo data may include the physiological motion related data and data related to a rigid motion of the subject (hereinafter rigid motion related data). The one or more cameras 230 may be configured to acquire a plurality of image frames of the subject. In some embodiments, the rigid motion may be identified based on at least a part of the plurality of image frames. The processing device 240 may be configured to process data/signals acquired by the one or more cameras 230 and the one or more radars 220 (e.g., image data and radar echo data), and generate a control signal for controlling the scanner 210 to scan the subject. In some embodiments, the processing device 240 may be configured to reconstruct an image based on the scan data.

In some embodiments, the scanner 210 may include a CT device, an MRI device, a PET device, an ultrasonic device, an X-ray imaging device, or the like. In some embodiments, the medical device 220 may include a treatment device, e.g., a radiation treatment device, instead of the scanner 210. For example, the imaging device 200 may be the IGRT device. The following description is provided with reference to exemplary embodiments that the medical device include a scanner 210 for illustration purposes and not intended to be limiting.

The scanner 210 may include various suitable medical imaging devices for diagnosing and/or treating a disease, and not intended to be limiting. Taking the MRI device as an example, a magnetic resonance unit of the MRI device may include a magnet assembly, a gradient coil assembly, and a radiofrequency (RF) coil assembly. For example, the magnet assembly may generate a main magnetic field for polarizing the subject to be scanned. The gradient coil assembly may generate a gradient magnetic field. The RF coil assembly may include a plurality of RF coils for transmitting and/or receiving RF signals. In some embodiments, the magnetic resonance unit may form a cavity providing an examination space. The scanning table may move along the cavity. The subject may be placed on the scanning table for MR imaging.

In some embodiments, the radar of the one or more radars 220 may at least include an antenna and a processing component. In some embodiments, the antenna and the processing component may be integrated into a single chip. In some embodiments, the antenna and the processing component may be disposed separately. In some embodiments, the antenna may transmit radar signals to the subject within a coverage zone in a radar field. The antenna may receive radar echo signals reflected from the subject within the coverage zone. In some embodiments, a radar may include multiple antennas. The detection angle of the antenna may be adjusted according to the position of the subject or at a part of the subject. For example, a detectable region of the multiple antennas may be designed to cover the subject at suitable detection angles (e.g., 60 degrees, 70 degrees, 130 degrees, or 180 degrees) in order to acquire large-scale radar echo data. As another example, a detection region of at a part of the multiple antennas may be designed to cover a region of interest (ROI) of the subject in order to acquire radar echo data regarding the ROI (e.g., a thoracic and abdominal region). In some embodiments, the detection angle of the antenna may be a fixed angle (e.g., 60 degrees). In some embodiments, the radar may be a phased array radar having an antenna array forming by a plurality of antenna units. Each antenna unit may be controlled by a single phase shift switch. The phase beams may be synthesized by controlling the phase beam emitted by each antenna unit.

In some embodiments, the one or more radars 220 may be used to provide a non-invasive remote monitoring for the physiological motion. The one or more radars 220 may be disposed on various suitable positions for monitoring the physiological motion. For example, the one or more radars 220 may be disposed on a component of the scanner 210, such as, on an RF receiving coil, in a cavity around the examination space, or on a scanning table. As another example, the one or more radars 220 may be attached to the subject's clothes (e.g., the position close to the thoracic and abdominal region). In some embodiments, the one or more radars 220 may be disposed on a suitable position outside the medical device, such as, on a ceiling of a treatment room, on the floor of the treatment room, or a holder outside the medical device, etc.

In some embodiments, a distance between the radar and the subject may be 0-25 meters (e.g., less than 5 meters). Alternatively, the distance may be 1 millimeter to 3 meters, such as, 1 meter, or 2 meters. Alternatively, the distance may be 10 millimeters to 3000 millimeters, such as 100 millimeters to 2000 millimeters. The radar may emit radar beams (e.g., electromagnetic waves) to irradiate the subject, and receive radar echo signals reflected by the subject. In some embodiments, an emission frequency of the radar may be set as 1 GHz to 100 GHz. For example, a low frequency range (e.g., 1 GHz to 50 GHz) may be used to detect an interior movement inside the subject (e.g., a cardiac movement, a diaphragm movement). A high frequency range of the radar (e.g., 50 GHz to 100 GHz) may be used to detect a body surface movement (e.g., a skin movement). In some embodiments, the emission frequency of the radar may be set as different frequency ranges so as to identify various movements regarding the subject.

In some embodiments, the one or more radars 220 may include a single-mode radar and/or a multi-mode radar. For example, the single-mode radar may include a continuous wave (CW) radar, a non-continuous wave radar (e.g., a ultra wideband (UWB) radar, or a frequency modulated continuous wave (FMCW) radar), a LIDAR, and so on. The multi-mode radar may include a CW-UWB radar, a CW-FMCW radar, or a UWB-FMCW radar, and so on. The types of the radar may be adjusted according to different scenarios. For example, the CW radar may be activated to monitor the cardiac motion. As another example, the UWB radar may be activated to monitor the abdominal movement. As a further example, a combined use of the CW radar and the UWB radar may be used to detect the radiation in various wavebands (e.g., in the millimeter wavelength range) that is emitted or reflected by the subject.

In some embodiments, the one or more radars 220 may be configured to detect radar echo signals from the subject. The radar echo signals may include motion information regarding the subject (e.g., rigid motion information and/or physiological motion information). For example, the rigid motion may include a translational and/or rotational motion of the subject. Exemplary rigid motion may include a pose motion of the subject, such as the rotating or nodding of the head of the subject, legs motion, hands motion, and so on. As another example, the physiological motion may include respiratory motion (or breathing motion), heart motion (or cardiac motion), and so on. In some embodiments, the radar echo signals may be image data or point cloud data. For example, the radar echo signals may be a three-dimensional image data regarding the head of the subject. As another example, the radar echo signals may be point cloud data including location information of one or more characteristic points (e.g., the highest point coordinates and the lowest point coordinates of the abdominal). In some embodiments, the radar echo signals may be desired to determine physiological motion of the subject. One or more parameters (e.g., cardiac motion data or respiratory motion data) of the physiological motion may be used to control the scan of the medical device, which may reduce or avoid motion artifacts (e.g., motion artifacts caused by the cardiac motion or the breathing motion) in a reconstructed image. However, the radar echo signals may include disturbed signals caused by the rigid motion of the subject. The disturbed signals may be filtered in a subsequent processing operation. The use of the one or more radars 220 may be an effective physiological motion detection means instead of conventional means. For example, the conventional means may require one or more electrodes and/or respiratory zones attached to the body of the subject in order to detect the physiological motion of the subject, which may cause more or less discomfortable feeling for some subjects. By contrast, the use of the radar may reduce the discomfortable feeling, and ignore an installing time of the electrodes and/or respiratory zones, which may reduce the scan time of the medical device.

In some embodiment, the design of the one or more cameras 230 may aim at obtaining rigid motion information. The camera of the one or more cameras 230 may include a three-dimensional (3D) camera, such as a time of flight (TOF) camera, a structural light camera, a binocular camera, a LIDAR camera, or the like, or any combination thereof. The 3D camera may be configured to capture position and/or depth information of an object. The 3D image or model may be reconstructed based on the captured position and/or depth information. It should be noted that light signals captured by the camera do not interfere with the radar echo signals captured by the radar. In some embodiments, the one or more cameras 230 may include various commercially available image capture devices for imaging. For example, the one or more cameras 230 may be configured to generate video images of the subject. The video images may include a sequence of image frames of the subject. The rigid motion may be identified by analyzing the sequence of image frames. In some embodiments, motion parameters regarding the rigid motion may be used to correct the radar echo data captured by the one or more radars 220. The corrected radar echo data may be used to generate accurate physiological information.

In some embodiments, the one or more cameras 230 may be disposed on various suitable positions for monitoring the rigid motion of the subject. For example, the one or more cameras 230 may be disposed on a component of the scanner 210, such as, on an RF receiving coil, in a cavity around the examination space, or on a scanning table. In some embodiments, the one or more cameras 230 and the one or more radars 220 may be disposed at the same position in the examination space of the scanner 210. In some embodiments, the one or more cameras 230 and the one or more radars 220 may be disposed at different positions, respectively. For example, the one or more radars 220 may be disposed in the cavity, and the one or more cameras 230 may be disposed on the RF receiving coil. In some embodiments, positions of the one or more cameras 230 and the one or more radars 220 may be adjusted according to the position of the subject, in order to detect corresponding signals from the subject within their coverage zone. The use of one or more cameras 230 is also a non-contactless detection for the subject, which may reduce the discomfortable feeling of the subject by contract with the contactless detection. In some embodiments, the one or more cameras 230 may be aligned at a certain angle towards the subject or at least a part of the subject, in order to obtain a larger detection angle and a large-scale detection data.

In some embodiments, the radar and the camera may be integrated into a radar-camera sensor module (not shown in FIG. 2). The integrated radar-camera sensor module includes a radar component for transmitting radar signals and receiving reflected radar signals (i.e., radar echo signals) that are reflected from one or more objects within a coverage zone in a radar field. The integrated radar-camera sensor module further includes a camera component for capturing images based on light waves that are seen and captured within a coverage zone in a camera field. In some embodiments, the radar component and the camera component may be housed in a common housing. The common housing may be made of various materials, such as rigid materials, or non-rigid materials. In some embodiments, the radar component and the camera component may be coupled to processing circuits for processing the captured images and the received reflected radar signals, such as, fusing the captured images and the reflected radar signals. The fused data may be used to indicate vital signs of the subject, such as respiratory motion, heart motion.

In some embodiments, the camera component may include a plurality of optical elements and an imager. The camera component may include a commercially available image capture device for imaging. For example, the camera component may be configured to generate video images of the subject. The video images may include a plurality of image frames. In some embodiments, the radar component may include a radar transceiver coupled to an antenna. The transceiver and antenna operate to transmit radar signals within the desired coverage zone, and to receive radar echo signals reflected from the subject within the coverage zone. In some embodiments, the radar component may transmit a single fan-shaped radar beam and form multiple beams by receiving digital beamforming. In some embodiments, the antenna may include a vertical polarization antenna and/or a horizontal polarization antenna. The vertical polarization antenna may provide vertical polarization of the radar signals. The horizontal polarization antenna may provide horizontal polarization of the radar signals.

Figure 3:
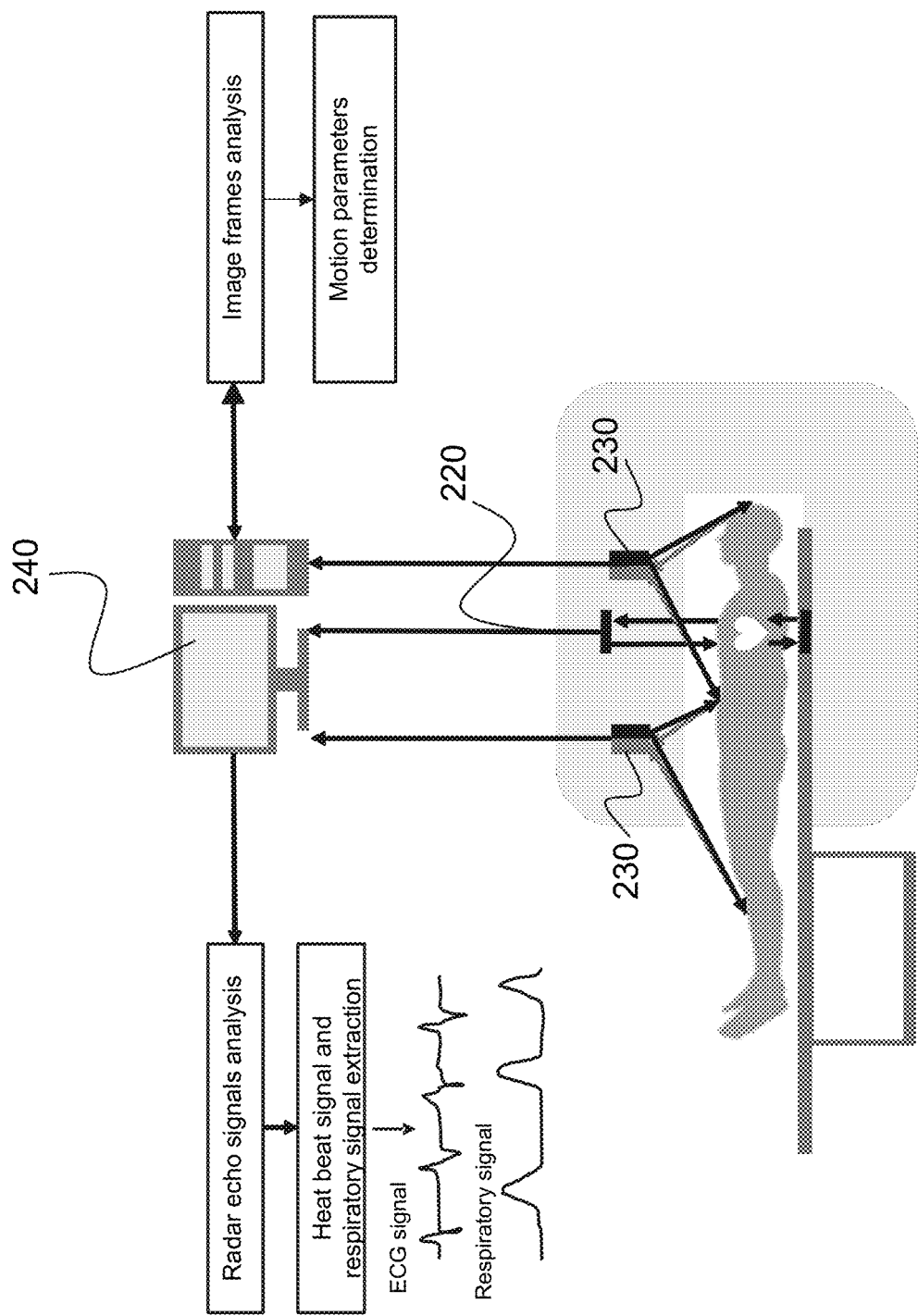
FIG. 3 is a schematic diagram illustrating an exemplary work scheme according to some embodiments of the present disclosure.

FIG. 3 is a schematic diagram illustrating an exemplary work scheme according to some embodiments of the present disclosure. As shown in FIG. 3, a radar 220 and two cameras 230 may be arranged in the examination space of the medical device. The radar 220 may be configured to acquire radar echo signals from the subject. The radar echo signals may provide information related to physiological motion of the subject (e.g., respiratory motion, or heart motion). In some cases, the radar echo signals may include disturbed signals caused by rigid motion of the subject (e.g., a head movement, leg movement, hand movement, etc). The two cameras 230 may be configured to capture a plurality of image frames included the subject. The plurality of image frames may provide information related to rigid motion of the subject. In some embodiments, the processing device 240 may perform one or more fusion operations for the plurality of image frames and the radar echo signals. For example, the one or more fusion operations may include image frames analysis and radar echo signals analysis. In some embodiments, the processing device 240 may perform the image frames analysis to determine one or more motion parameters regarding the rigid motion. The determined motion parameters may be transformed into a coordinate system corresponding to the radar 220. In some embodiments, the processing device 240 may perform the radar echo signals analysis to determine data related to the physiological motion, such as heart beat signal and/or respiratory signal as shown in FIG. 3. In some embodiments, the heart beat signal may be an electrocardiogram (ECG) signal. In some embodiments, the radar echo signal analysis may include one or more operations for correcting the radar echo signals based on the motion parameters regarding the rigid motion. For example, the processing device 240 may correct the radar echo signals by filtering out the disturbed signals caused by the rigid motion, and extract the heart beat signals (e.g., ECG signals) and the respiratory signals. In some embodiments, the extracted heat beat signals and/or respiratory signals may be used to control one or more scan operations of the medical device (e.g., the MRI device). In some embodiments, the processing device 240 may reconstruct a medical image (e.g., an MR image) based on the scan data acquired by the medical device (e.g., the MRI device). More descriptions about the image frames analysis and the radar echo signal analysis may be found elsewhere in the present disclosure (e.g., FIG. 7A and FIG. 8, and the descriptions thereof).

Figure 4:
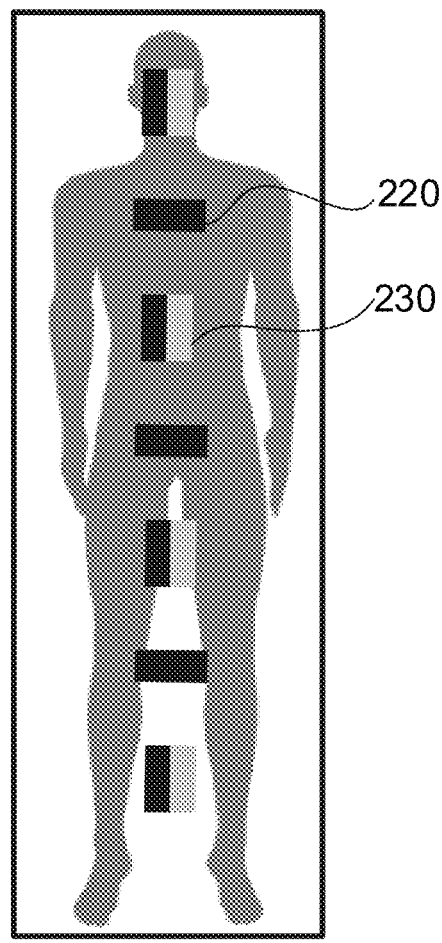
FIG. 4 is a schematic diagram illustrating an exemplary data acquisition according to some embodiments of the present disclosure.

FIG. 4 is a schematic diagram illustrating an exemplary data acquisition according to some embodiments of the present disclosure. In some embodiments, the one or more radars 220 and the one or more cameras 230 may acquire corresponding data simultaneously in response to a clock signal from a system clock of the medical device. In some embodiments, as illustrated in FIG. 4, the one or more radars 220 and the one or more cameras 230 may alternately capture corresponding data regarding various parts of the subject at different time points. In some embodiments, the detection angles of the one or more cameras 230 and the one or more radars 220 may be set according to a region of interest (ROI) of the subject. The ROI of the subject may be any part of the subject, such as, the head, the chest, a leg, and so on. For example, when the ROI is the chest region, the detection angle of the camera may be set as 60 degrees, and the detection angle of the radar may be set as 90 degrees.

The one or more cameras 230 and the one or more radars 220 may acquire data within their own coverage zone. The acquired data may be used to characterize the motion of the subject (e.g., the physiological motion, or the rigid motion).

Figure 5:
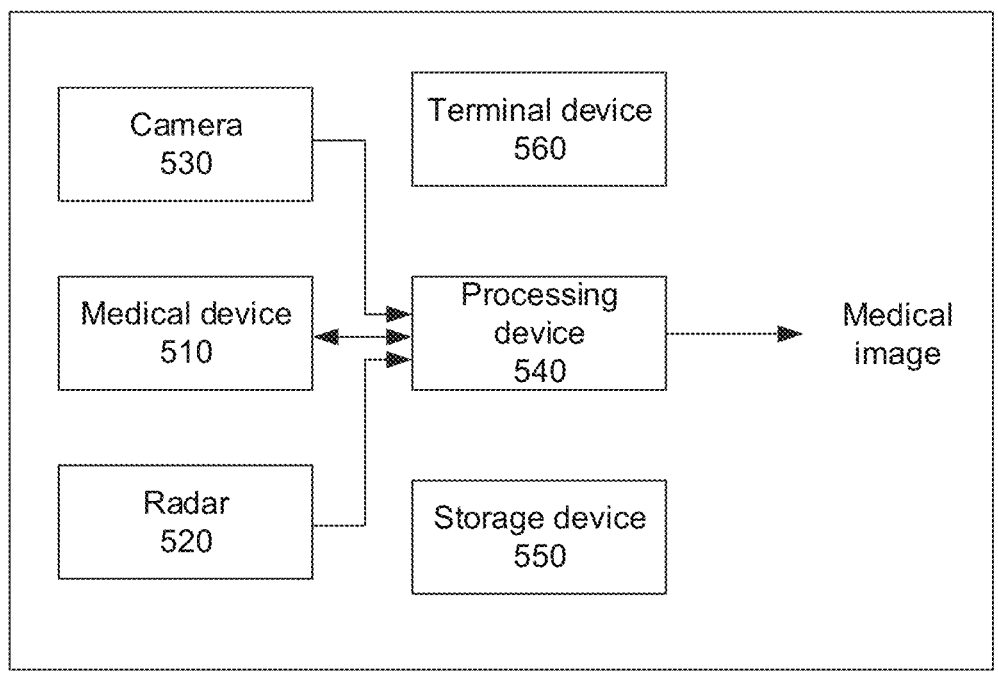
FIG. 5 is a block diagram illustrating an exemplary medical imaging system according to some embodiments of the present disclosure.

FIG. 5 is a block diagram illustrating an exemplary medical imaging system according to some embodiments of the present disclosure. As illustrated in FIG. 5, the medical imaging system 500 may include a medical device 510, a radar 520, a camera 530, a processing device 540, a storage device 550 and a terminal device 560. In some embodiments, the medical device 510 may scan a subject or at a part of the subject (e.g., an ROI of the subject). The radar 520 may acquire radar echo signals from the subject. The camera 530 may acquire a plurality of image frames including the subject. The processing device 540 may process the radar echo signals and the plurality of image frames to generate a control signal for controlling the medical device. In response to the control signal, the medical device 510 may obtain accurate scan data. The processing device 540 may reconstruct a medical image based on the scan data. In some embodiments, one or more components of the medical imaging system 500 (e.g., the camera 530, the radar 520 or the medical device 510) may be connected by various means. For example, the medical device 510, the radar 520, the camera 530, the terminal device 560 and/or the storage device 550 may be connected to the processing device 540 via a network (e.g., the network 150), or be connected to the processing device 540 directly.

In some embodiments, the medical device 510 may be used in medical treatments and/or diagnosis. The medical device 510 may be the same as or similar to the medical device 110 as illustrated in FIG. 1. Taking the IGRT device as an example, the IGRT device may irradiate a target (e.g., a lesion (or a tumor)) using various radioactive rays, such as, X-rays, γ-rays, electron lines, proton beams, and so on. The IGRT device may include an accelerator (e.g., a linear accelerator or a cyclotron). The linear accelerator may generate and emit the radioactive rays (e.g., X-rays) to the target for killing cancer cells. A therapeutic effect on the tumor may be achieved. The accelerator may rotate with a gantry of the IGRT device in the clockwise or counterclockwise direction around an axis of the rack. The IGRT device may include a treatment table for supporting the subject. In some embodiments, the treatment table may be a six-dimensional platform capable of performing a linear motion in three directions of x, y, and z, and a rotational motion in three directions of x, y, and z. The treatment table may move the subject to a corresponding position (e.g., a target zone) accurately and/or quickly.

In some embodiments, the radar 520 may be the same as or similar to the radar 220. For example, the radar 520 may include a single-mode radar and/or a multi-mode radar. For example, the single-mode radar may include a continuous wave (CW) radar, a non-continuous wave radar (e.g., an ultra wideband (UWB) radar, or a frequency modulated continuous wave (FMCW) radar), a light detection and ranging (LIDAR) device, and so on. The multi-mode radar may include a CW-UWB radar, a CW-FMCW radar, or an UWB-FMCW radar, and so on. In some embodiments, the camera 530 may be the same as or similar to the camera 230. For example, the camera may include a three-dimensional (3D) camera, such as a time of flight (TOF) camera, a structured light camera, a binocular camera, a LIDAR camera, or the like, or any combination thereof. More descriptions of the radar and the camera may be found elsewhere in the present disclosure. See, e.g., FIG. 2, and the descriptions thereof.

In some embodiments, the processing device 540 may process data and/or information obtained from the medical device 510, the terminal device 560, the storage device 550, the camera 530, and/or the radar 520. For example, the processing device 540 may determine first data regarding a first motion of the subject. The first motion may include a rigid motion of the subject. The first data may be rigid motion related data, such as, motion parameters. As another example, the processing device 540 may determine second data regarding a second motion of the subject. The second motion may include a physiological motion of the subject. The second data may be physiological motion related data, such as cardiac motion data or respiratory motion data. As a further example, the processing device 540 may generate a control signal for controlling the device based on the first data and the second data. In some embodiments, the processing device 540 may be the same as or similar to the processing device 120 illustrated in FIG. 1. For example, the processing device 540 may be a single server or a server group. As another example, the processing device 540 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the storage device 550 may store data and/or instructions. In some embodiments, the storage device 550 may store data obtained from medical device 510, the radar 520, the camera 530, the processing device 540, and the terminal device 560. In some embodiments, the storage device 550 may store data and/or instructions that the processing device 540 may execute or use to perform exemplary methods described in the present disclosure. The storage device 550 may be the same as or similar to the storage device 130 illustrated in FIG. 1. For example, the storage device 550 may include a mass storage device, a removable storage device, a volatile read-and-write memory, a read-only memory (ROM), or the like, or any combination thereof.

In some embodiments, the terminal device 560 may be connected to and/or communicate with the medical device 510, the radar 520, the camera 530, the processing device 540 and/or the storage device 550. For example, the terminal device 560 may obtain a processed image from the processing device 540. As another example, the terminal device 560 may obtain scan data acquired by the medical device 510 and transmit the scan data to the processing device 540 to be processed. In some embodiments, the terminal device 560 may be the same as or similar to the terminal(s) 140 illustrated in FIG. 1. For example, the terminal device 560 may include a mobile device, a tablet computer, a laptop computer, or the like, or any combination thereof.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 550 may be a data storage including cloud computing platforms, such as, a public cloud, a private cloud, a community cloud, and a hybrid cloud, etc. However, those variations and modifications do not depart from the scope of the present disclosure.

Figure 6:
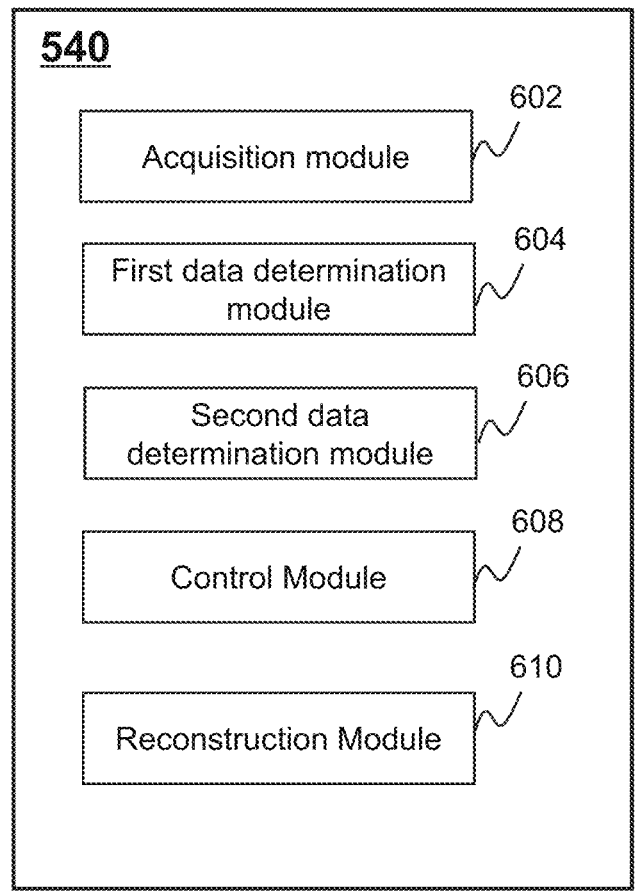
FIG. 6 is a block diagram illustrating an exemplary processing device according to some embodiments of the present disclosure.

FIG. 6 is a block diagram illustrating an exemplary processing device according to some embodiments of the present disclosure. In some embodiments, the processing device 540 may be in communication with a computer-readable storage medium (e.g., the storage device 550 illustrated in FIG. 5, the storage device 130 illustrated in FIG. 1) and may execute instructions stored in the computer-readable storage medium. The processing device 540 may include an acquisition module 602, a first data determination module 604, a second data determination module 606, a control module 608, and a reconstruction module 610.

The acquisition module 602 may be configured to acquire data from one or more modules of the processing device 540. In some embodiments, the acquisition module 602 may obtain first data regarding a first motion of a subject in an examination space of a medical device. In some embodiments, the first data determination module 604 may determine the first data regarding the first motion. The acquisition module 602 may obtain the first data from the first data determination module 604. In some embodiments, the acquisition module 602 may acquire a plurality of image frames of the subject through one or more cameras. The one or more cameras may be installed on the medical device. The plurality of image frames may be used to determine the first data. In some embodiments, the acquisition module 602 may obtain second data regarding a second motion of the subject. In some embodiments, the second data determination module 606 may determine the second data regarding the second motion of the subject. The acquisition module 602 may obtain the second data from the second data determination module 606. In some embodiments, the acquisition module 602 may acquire radar echo data through one or more radars. The one or more radars may be installed on the medical device. The radar echo data may be used to determine the second data. In some embodiments, the first motion may include a rigid motion, and the second motion may include a physiological motion.

The first data determination module 604 may determine, based on at least a part of the plurality of image frames, first data including one or more motion parameters. For example, the first data determination module 604 may process the plurality of image frames to identify the rigid motion of the subject. For example, the first data determination module 604 may determine one or more motion parameters of the first motion based on at least a part of the plurality of image frames. In some embodiments, the one or more motion parameters may include a three-dimensional translation matrix and/or a three dimensional rotation matrix. In some embodiments, the first data determination module 604 may determine the one or more motion parameters using an image registration technique. Exemplary image registration technique may include but not limited to a pixel-based registration algorithm, a feature-based registration algorithm, a contour-based registration algorithm, a mutual information-based registration algorithm, and so on. More descriptions of the determination of the first data may be found elsewhere in the present disclosure (e.g., FIG. 8 and the description thereof).

The second data determination module 606 may determine the second data regarding the second motion of the subject. In some embodiments, the second motion may include a physiological motion of the subject. The physiological motion may include a heart motion and/or respiratory motion of the subject. In some embodiments, the second data determination module 606 may process the radar echo data to identify the physiological motion of the subject. For example, the second data determination module 606 may correct the acquired radar echo data by filtering out disturbed information caused by the rigid motion. The second data determination module 606 may extract the second data from the corrected radar echo data. The second data may include cardiac motion data or respiratory motion data. More descriptions of the determination of the second data may be found elsewhere in the present disclosure (e.g., FIG. 8 and the description thereof).

The control module 608 may generate, based on the first data and the second data, a control signal for controlling the medical device to scan at least a part of the subject. More specifically, the control module 608 may generate the control signal based on the cardiac motion data and/or the respiratory motion data. The cardiac motion data and/or the respiratory motion data may be determined based on the first data and the second data. In some embodiments, the control module 608 may generate the control signal using a gating technique. The gating technique may include a cardiac gating and a respiratory gating. In response to the control signal, the medical device may be directed to scan the subject or at least a part of the subject.

The reconstruction module 610 may reconstruct a medical image based on the scan data acquired by the medical device. For example, the reconstruction module 610 may reconstruct the image using one or more reconstruction algorithms. The one or more reconstruction algorithms may include but not limited to a 2-dimensional Fourier transform technique, a back projection technique (e.g., a convolution back projection technique, a filtered back projection technique), an iteration reconstruction technique, etc. Examples of iterative reconstruction techniques may include a simultaneous algebraic reconstruction technique (SART), a simultaneous iterative reconstruction technique (SIRT), an ordered subset convex technique (OSC), ordered subset maximum likelihood methodologies, an ordered subset expectation maximization (OSEM) methodology, an adaptive statistical iterative reconstruction technique (ASIR) methodology, a least squares QR methodology, an expectation maximization (EM) methodology, an OS-separable paraboloidal surrogates technique (OS-SPS), an algebraic reconstruction technique (ART), a Kacsmarz reconstruction technique, or any other iterative reconstruction technique or methodology that meets application-specific requirements.

It should be noted that the descriptions above in relation to processing device 540 are provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. In some embodiments, the processing device 540 may include one or more other modules. For example, the processing device 540 may include a storage module to store data generated by the modules in the processing device 540. In some embodiments, any two of the modules may be combined as a single module, and any one of the modules may be divided into two or more units.

Figure 7A:
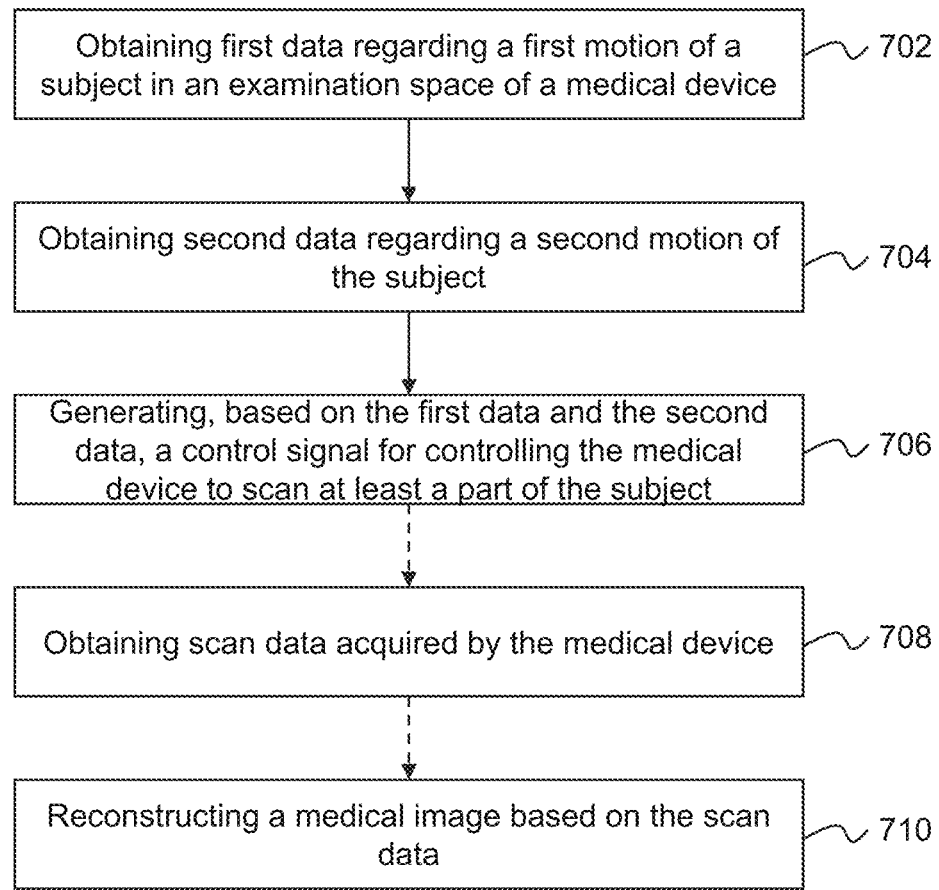
FIG. 7A is a flowchart illustrating an exemplary process for controlling a medical device according to some embodiments of the present disclosure.

FIG. 7A is a flowchart illustrating an exemplary process for controlling a medical device according to some embodiments of the present disclosure. Process 700 may be implemented in the medical system 100 illustrated in FIG. 1 or the medical imaging system 500 illustrated in FIG. 5. For example, the process 700 may be stored in the storage device 130 and/or the storage device 550 in the form of instructions (e.g., an application), and invoked and/or executed by the processing device 120 (e.g., the processing device 540 illustrated in FIG. 5, or one or more modules in the processing device 540 illustrated in FIG. 6). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 702, the processing device (e.g., the acquisition module 602 of the processing device 540) may obtain first data regarding a first motion of a subject in an examination space of a medical device. In some embodiments, the first data determination module 604 of the processing device 540 may determine the first data regarding the first motion of the subject in the examination space of the medical device. The acquisition module 602 may obtain the first data from the first data determination module 604. In some embodiments, the first motion may refer to a rigid motion. The rigid motion may include a translational and/or rotational motion of the subject. Exemplary rigid motion may include a pose motion of the subject, such as the rotating or nodding of the head of the subject, a motion of a leg, a motion of a hand, and so on. The first data may refer to data related to the first motion (e.g., the rigid motion). Hereinafter the first data may be referred to as first motion related data, rigid motion related data, or pose motion related data.

In some embodiments, the acquisition module 602 may acquire, via one or more cameras (e.g., the one or more cameras 230, or the camera 530), a plurality of image frames regarding the first motion of the subject in the examination space of the medical device. The one or more cameras may capture the plurality of image frames including the subject. The plurality of image frames may be sent to the acquisition module 602. The first data determination module 604 may process the plurality of image frames to identify the rigid motion of the subject. For example, the first data determination module 604 may determine one or more motion parameters of the first motion based on at least a part of the plurality of image frames. In some embodiments, the one or more motion parameters may include a three-dimensional translation matrix and/or a three dimensional rotation matrix. In some embodiments, the first data determination module 604 may determine the one or more motion parameters using an image registration technique. Exemplary image registration techniques may include a pixel-based registration algorithm, a feature-based registration algorithm, a contour-based registration algorithm, a mutual information-based registration algorithm, and so on. More descriptions of the determination of the first data may be found elsewhere in the present disclosure (e.g., FIG. 8 and the description thereof).

In 704, the processing device (e.g., the acquisition module 602 of the processing device 540) may obtain second data regarding a second motion of the subject. In some embodiments, the second data determination module 606 of the processing device 540 may determine the second data regarding the second motion of the subject. The acquisition module 602 may obtain the second data from the second data determination module 606. In some embodiments, the second motion may include a physiological motion of the subject. The physiological motion may include a cardiac motion, a respiratory motion, or the like, of the subject. The second data may refer to data related to the second motion (e.g., the physiological motion). Hereinafter the second data may be referred to as second motion related data, or physiological motion related data.

In some embodiments, the acquisition module 602 may acquire, via one or more radars (e.g., the one or more radars 220, or the radar 520), radar echo data from the subject. For example, the one or more radars may emit radar signals to the subject or at least a part of the subject, and receive the radar echo signals reflected from the subject. The radar echo signals may include motion information of the subject. The motion information may include not only the physiological motion information, but also the rigid motion information. In this case, the radar echo signals caused by the rigid motion may be designated as disturbed signals. The acquired radar echo data may be sent to the acquisition module 602. The second data determination module 606 may process the radar echo data to identify the physiological motion of the subject. For example, the second data determination module 606 may correct the acquired radar echo data by filtering out the disturbed information caused by the rigid motion. The second data determination module 606 may extract the second data from the corrected radar echo data. The second data may include cardiac motion data or respiratory motion data. More descriptions of the determination of the second data may be found elsewhere in the present disclosure (e.g., FIG. 8 and the description thereof).

In 706, the processing device (e.g., a control module 608 of the processing device 540) may generate, based on the first data and the second data, a control signal for controlling the medical device to scan at least a part of the subject. In some embodiments, the processing device 540 may generate accurate cardiac motion data and/or respiratory motion data based on the first data and the second data. The accurate cardiac motion data and respiratory motion data may facilitate to reduce or avoid motion artifacts (e.g., cardiac motion artifacts or respiratory motion artifacts) in a reconstructed image. For example, the second data determination module 606 may correct the radar echo data according to the one or more motion parameters of the first motion. The disturbed component of the radar echo data may be removed by the correction. The cardiac motion data and/or the respiratory motion data extracted from the corrected radar echo data may be more accurate than the uncorrected radar echo data. In some embodiments, the control module 608 may generate the control signal using a gating technique. The gating technique may be used for synchronization of signal (e.g., an MR signal) acquisition to the cardiac and/or respiratory cycle.

Figure 7B:
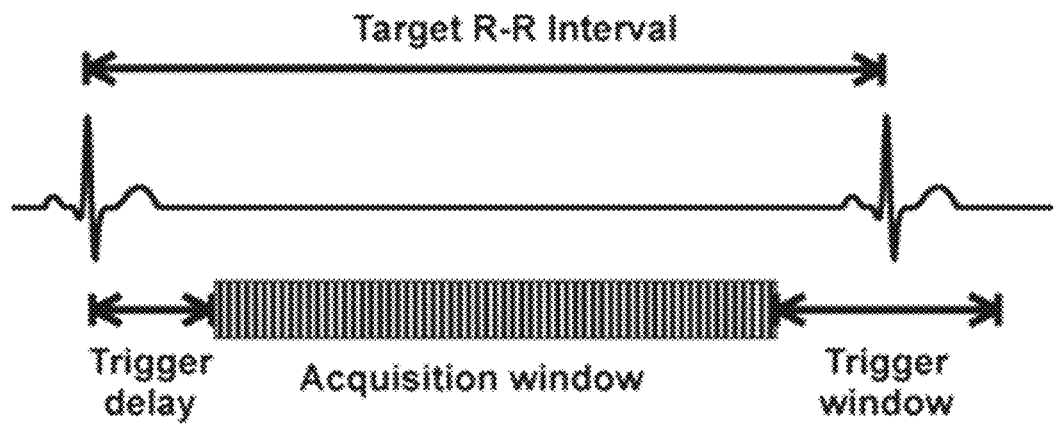
FIG. 7B is a schematic diagram illustrating an exemplary cardiac gating according to some embodiments of the present disclosure.

In some embodiments, the gating technique may include a cardiac gating and/or a respiratory gating. For example, the cardiac gating may be based on cardiac motion data (e.g., an ECG signal). The ECG signal may show a plurality of cardiac cycles. Each cardiac cycle may correspond to a heartbeat. In some embodiments, one cardiac cycle may be a time interval between two R-waves of the ECG signal. Merely by way of example, FIG. 7B illustrates an exemplary cardiac gating according to some embodiments of the present disclosure. As illustrated in FIG. 7B, in a specific time point between two R-waves (e.g., an end of a trigger delay, or a beginning of an acquisition window), the control module 608 may generate a control signal (e.g., a gating signal) for triggering the medical device (e.g., the MRI device) to scan in order to acquire scan data. The trigger delay may be defined as the time interval between the first R-wave and the beginning of data acquisition. The scan data may be acquired during the acquisition window. The control module 608 may generate the control signal for each scan based on the ECG signal. The use of the cardiac gating technique may facilitate to reduce or avoid the cardiac motion artifacts.

Figure 7C:
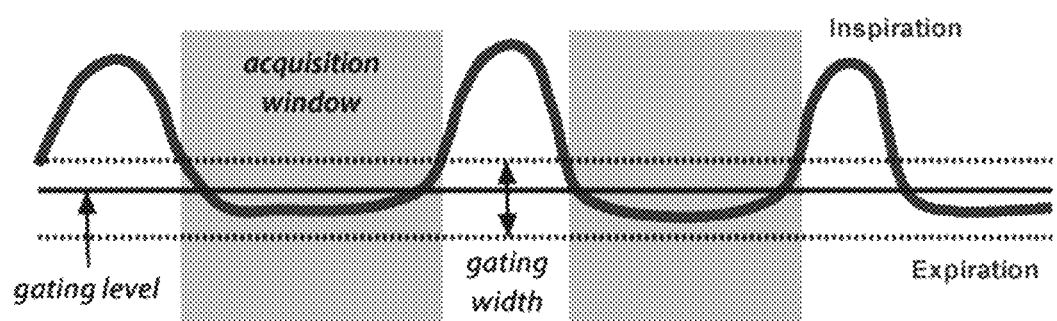
FIG. 7C is a schematic diagram illustrating an exemplary respiratory gating according to some embodiments of the present disclosure.

As another example, FIG. 7C illustrates an exemplary respiratory gating according to some embodiments of the present disclosure. The respiratory gating may be based on respiratory data. The respiratory data may show a plurality of respiratory cycles as shown in FIG. 7C. The respiratory cycle may be a cycle of inspiration and expiration. The acquisition window may be defined as a time interval when an amplitude of the respiratory signal is within the gating width. The scan data may be acquired during the acquisition window. In some embodiments, when the amplitude of the respiratory signal is within the gating width, the control module 608 may generate a control signal (e.g., a gating signal) for triggering the medical device (e.g., the MRI device) to scan and acquiring scan data during expiration (when least diaphragmatic movement occurs).

In some embodiments, the gating technique may be used to control various medical devices for reducing motion artifacts. For example, an ECG-gated technique may be used to perform a CT scan (e.g., for cardiac imaging). As another example, the respiratory and cardiac gating technique may be used to perform a PET scan (e.g., for cardiac PET imaging). As a further example, the respiratory gating may be used to monitor the movement of a tumor during normal breathing of a subject in a radiotherapy session. When the tumor moves outside a target field, a gating signal for turning off the treatment beam may be generated according to the respiratory gating.

In 708, the processing device (e.g., the acquisition module 602 of the processing device 540) may obtain scan data acquired by the medical device. For example, in response to the control signal, the medical device may be directed to scan the subject or at least part of the subject. In some embodiments, the scan data may be stored in the storage device 130. The acquisition module 602 may send the scan data to the reconstruction module 610 for further processing.

In 710, the processing device (e.g., the reconstruction module 610 of the processing device 540) may reconstruct a medical image based on the scan data. In some embodiments, the reconstruction module 610 may reconstruct the image using one or more reconstruction algorithms. For example, the one or more reconstruction algorithms may include a 2-dimensional Fourier transform technique, a back projection technique (e.g., a convolution back projection technique, a filtered back projection technique), an iteration reconstruction technique, etc. Examples of iterative reconstruction techniques may include a simultaneous algebraic reconstruction technique (SART), a simultaneous iterative reconstruction technique (SIRT), an ordered subset convex technique (OSC), ordered subset maximum likelihood methodologies, an ordered subset expectation maximization (OSEM) methodology, an adaptive statistical iterative reconstruction technique (ASIR) methodology, a least squares QR methodology, an expectation maximization (EM) methodology, an OS-separable paraboloidal surrogates technique (OS-SPS), an algebraic reconstruction technique (ART), a Kacsmarz reconstruction technique, or any other iterative reconstruction technique or methodology that meets application-specific requirements.

It should be noted that the description of the process 700 is provided for the purposes of illustration, and not intended to limit the scope of the present disclosure. For persons having ordinary skills in the art, various variations and modifications may be conducted under the teaching of the present disclosure. For example, operations 702 and 704 may be integrated into a single operation. As another example, operations 704 and 706 may be integrated into a single operation. However, those variations and modifications may not depart from the protecting of the present disclosure.

Figure 8:
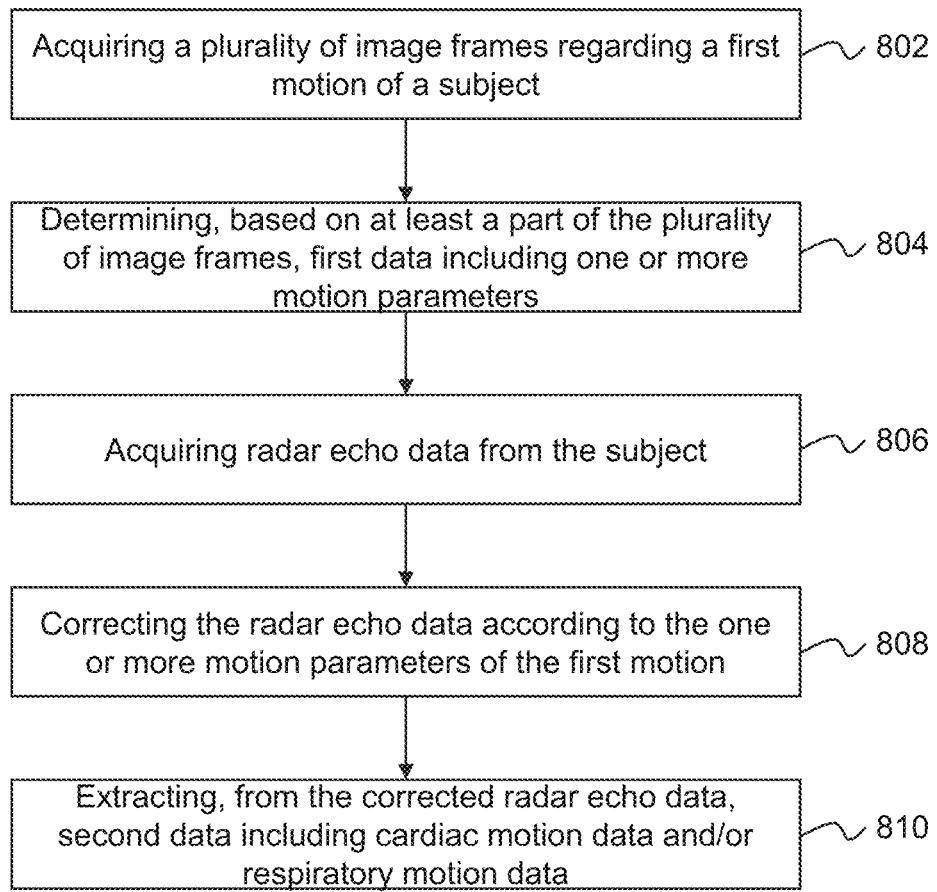
FIG. 8 is a flowchart illustrating an exemplary process for extracting physiological motion related data according to some embodiments of the present disclosure.

FIG. 8 is a flowchart illustrating an exemplary process for extracting physiological motion related data according to some embodiments of the present disclosure. Process 800 may be implemented in the medical system 100 illustrated in FIG. 1 or the medical imaging system 500 illustrated in FIG. 5. For example, the process 800 may be stored in the storage device 130 and/or the storage device 550 in the form of instructions (e.g., an application), and invoked and/or executed by the processing device 120 (e.g., the processing device 540 illustrated in FIG. 5, or one or more modules in the processing device 540 illustrated in FIG. 6). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 802, the processing device (e.g., the acquisition module 602 of the processing device 540) may acquire a plurality of image frames regarding a first motion of a subject.

In some embodiments, the first motion may refer to a rigid motion. The rigid motion may include a translational and/or rotational motion of the subject. Exemplary rigid motion may include a pose motion of the subject, such as the rotating or nodding of the head of the subject, leg motion, hand motion, and so on. The rigid motion may be identified by a sequence of image frames. In some embodiments, one or more cameras (or other image capture devices) installed on the medical device (e.g., the medical device 110 or the medical device 510) may capture the sequence of image frames of the subject. The one or more cameras may be installed on suitable positions of the medical device in order to capture the sequence of image frames of the subject. In some embodiments, the captured image frames may be stored in a storage device (e.g., the storage device 130 or the storage device 550). The acquisition module 602 may acquire the image frames from the storage device.

In 804, the processing device (e.g., the first data determination module 604 of the processing device 540) may determine, based on at least a part of the plurality of image frames, first data including one or more motion parameters.

In some embodiments, the first data may refer to data related to the first motion (e.g., the rigid motion). In some embodiments, the first data determination module 604 may determine the one or more motion parameters according to the at least a part of the plurality of image frames. The one or more motion parameters may include a three-dimensional translation matrix and/or a three dimensional rotation matrix. The rigid motion (i.e., the first motion) may be measured by the one or more motion parameters.

In some embodiments, the one or more motion parameters may be determined using a tracking marker. Specifically, the tracking marker may be fixed on the subject or an ROI of the subject during the scan of the medical device. The tracking marker may be represented as a specific image texture in an image frame. In some embodiments, the rigid motion of the subject may be identified by tracking the motion of the tracking marker in at least two of the plurality of image frames. The first data determination module 604 may segment the tracking marker and the subject (or the ROI of the subject) from the image frame. The first data determination module 604 may obtain coordinates of the tracking marker in different image frames, respectively. The obtained coordinates are the coordinates in the camera coordinate system (hereinafter camera coordinates related to the tracking marker). The first data determination module 604 may determine the motion parameters based on the camera coordinates related to the tracking marker in different image frames.

Assuming that $f_0$ denotes a first image frame captured at the time point $t_0$, $f_1$ denotes a second image frame captured at the time point $t_1$. $X_{c0}$ denotes the coordinates related to the tracking marker at $t_0$, and $X_{c1}$ denotes the coordinates related to the tracking marker at $t_1$. Let $R_c$ be a rotation matrix and $T_c$ be a translation matrix for the rigid motion of the tracking marker between $t_0$ and $t_1$, respectively. The rigid motion may be described by Equation (1) as follows:

$$X_{c1} = R_c X_{c0} + T_c. \tag{1}$$

In some embodiments, $X_{c0}$ and $X_{c1}$ may be a 3×N dimensional matrix, where N denotes the number (or count) of the tracking marker(s). In some embodiments, Equation (2) may be introduced to determine $R_c$ and $T_c$:

$$C = [X_{c0} - \overline{X_{c0}}][X_{c1} - \overline{X_{c1}}], \tag{2}$$

where $\overline{X_{c0}}$ and $\overline{X_{c1}}$ are mean coordinate matrices of N tracking markers, respectively. In some embodiments, the first data determination module 604 may solve Equation (2) using, e.g., singular value decomposition (SVD). $R_c$ and $T_c$ may be determined based on the solutions of Equation (2). In some embodiments, if $R_c$ and $T_c$ are zero matrices, then no rigid motion exists between the time points $t_0$ and $t_1$. In other words, the subject did not move between the time points $t_0$ and $t_1$. In some embodiments, if at least one of $R_c$ and $T_c$ is a non-zero matrix, there may exist rigid motion between the time points $t_0$ and $t_1$. In other words, the subject may have moved between the time points $t_0$ and $t_1$. The rigid motion may be identified based on the motion parameters. In some embodiments, the rigid motion related data (e.g., the motion parameters) may be fed back to the one or more radars.

In 806, the processing device (e.g., the acquisition module 602 of the processing device 540) may acquire radar echo data from the subject. In some embodiments, the radar echo data and the plurality of image frames may be acquired simultaneously by the one or more radars and the one or more cameras, respectively. That is, the operation 802 and the operation 806 may be performed simultaneously.

In some embodiments, the acquisition module 602 may acquire the radar echo data acquired by the one or more radars in real time. Exemplary radars may include a continuous wave (CW) radar, an ultra wideband (UWB) radar, or a frequency modulated continuous wave (FMCW) radar, and so on. The one or more radars may be installed at suitable positions on or in the vicinity of the medical device in order to capture radar echo signals indicative of the physiological motion (i.e., the second motion) of the subject. In some embodiments, the captured radar echo data may be stored in a storage device (e.g., the storage device 130 or the storage device 550). The acquisition module 602 may acquire the radar echo data from the storage device 130. In some embodiments, the one or more radars may detect both the physiological motion and the rigid motion if there exists the rigid motion during the scan. In this case, if the radar echo data without a correction is used to determine a physiological motion related data directly, the determined physiological motion related data may be inaccurate because the radar echo data includes disturbed information caused by the rigid motion.

In 808, the processing device (e.g., the second data determination module 606 of the processing device) may correct the radar echo data according to the one or more motion parameters of the first motion (e.g., the rigid motion).

The determined one or more motion parameters, based on Equation (1) and Equation (2), correspond to the camera coordinate system. To correct the radar echo data, the one or more motion parameters in the camera coordinate system may be transformed into the radar coordinate system. In some embodiments, system calibration between the camera coordinate system and the radar coordinate system may be performed.

Figure 9:
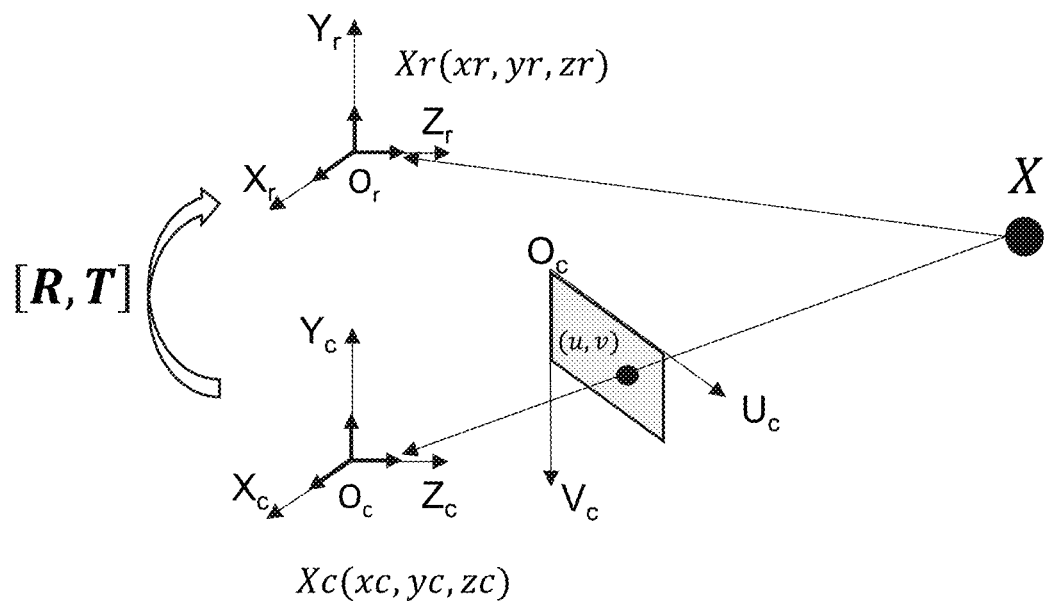
FIG. 9 is a schematic diagram illustrating an exemplary system calibrating according to some embodiments of the present disclosure.

Merely by way of example, FIG. 9 illustrates an exemplary system calibration between the camera coordinate system and the radar coordinate systems according to some embodiments of the present disclosure. As shown in FIG. 9, let $O_cX_cY_cZ_c$ be the camera coordinate system, and let $O_rX_rY_rZ_r$ be the radar coordinate system. The system calibration may be described by Equation (3) as follows:

$$X_r = R_{cr}X_c + T_{cr}, \quad (3)$$

where $X_r$ denotes the coordinates in the radar coordinate system, $X_c$ denotes the coordinates in the camera coordinate system, $R_{cr}$ denotes the rotation matrix between the camera coordinate system and the radar coordinate system, and $T_{cr}$ denotes the translation matrix between the camera coordinate system and the radar coordinate system. In some embodiments, the second data determination module 606 may determine one or more motion parameters corresponding to the radar coordinates system (also referred to as second motion parameters) based on the one or more motion parameters corresponding to the camera coordinate system (also referred to as first motion parameters). The second motion parameters may include the rotation matrix $R_r$ and the translation matrix $T_r$ in the radar coordinate system. In some embodiments, because the second motion parameters and the radar echo data are in the same coordinate system, the second data determination module 606 may correct the radar echo data based on the second motion parameters. For example, the second data determined module 606 may determine disturbed information corresponding to the second motion parameters, and correct the radar echo data by filtering out the disturbed information.

Assuming that $X_{r0}$ denotes the coordinates of a tracking marker in the radar coordinate system at $t_0$, and $X_{r1}$ denotes the coordinates of the tracking marker in the radar coordinate system at $t_1$. Thus, $$X_{r0} = R_{cr}X_{c0} + T_{cr}, \quad (4) \text{ and}$$

$$X_{r1} = R_{cr}X_{c1} + T_{cr}. \quad (5)$$

In some embodiments, $X_{r1}$ may be described by combining Equation (1) and Equation (4):

$$X_{r1} = R_{cr}R_cR_{cr}^{-1}X_{r0} - R_{cr}R_cR_{cr}^{-1}T_{cr} + R_{cr}T_c + T_{cr} = R_rX_{r0} + T_r. \quad (6)$$

In some embodiments, the second data determination module 606 may determine the rotation matrix $R_r$ and the translation matrix $T_r$ in the radar coordinate system based on Equation (6). For example, $$R_r = R_{cr}R_cR_{cr}^{-1}, \text{ and } T_r = -R_{cr}R_cR_{cr}^{-1}T_{cr} + R_{cr}T_c + T_{cr}. \quad (7)$$

In 810, the processing device (e.g., the second data determination module 606 of the processing device) may extract, from the corrected radar echo data, the second data including cardiac motion data and/or respiratory motion data.

In some embodiments, the second data may refer to data related to the second motion (e.g., the physiological motion). The second data may include cardiac motion data (e.g., an ECG signal) and respiratory motion data. Specifically, the second data determination module 606 may extract, from the corrected radar echo data, the cardiac motion data and the respiratory motion data, respectively. For example, the second data determination module 606 may perform an oblique removal operation for the corrected radar echo data. The oblique removal operation may include: it mixes an input signal with a reference signal (a local oscillator signal with appropriate delay, the delay is usually estimated from the result of narrowband signal ranging); then each scattering point corresponds to a single frequency component after mixing, and a discrete fourier transformation (DFT) is performed for the mixed-frequency output signal. The second data determination module 606 may filter the radar echo data after the oblique removal. The filtered radar echo data may be amplified by an amplifier. The amplified radar echo data may be divided into the cardiac motion data and respiratory motion data by a signal separator (e.g., a demultiplexer). In some embodiments, the cardiac motion data and the respiratory motion data may be sent to the medical device for real time controlling the medical device.

Figure 10:
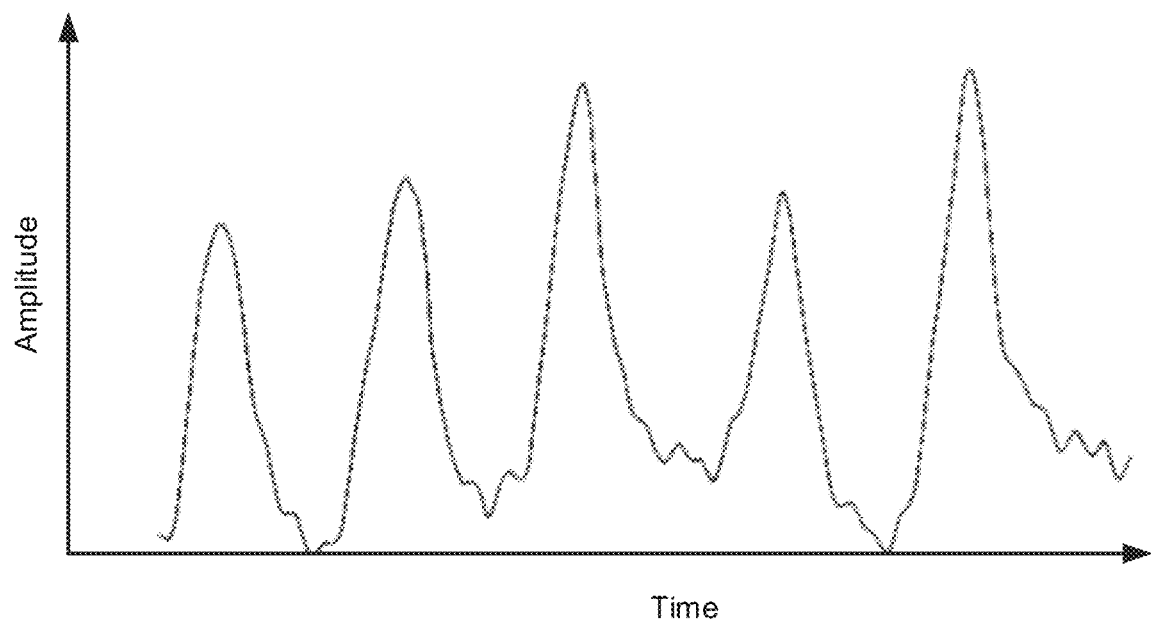
FIG. 10 is a schematic diagram illustrating an exemplary respiratory signal according to some embodiments of the present disclosure.
Figure 11:
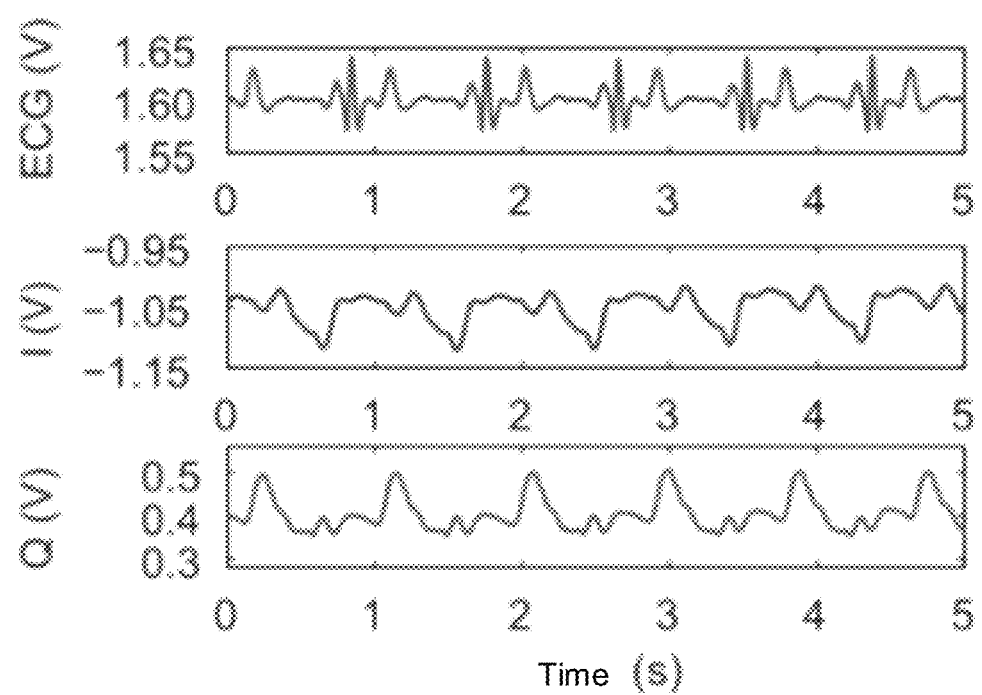
FIG. 11 is a schematic diagram illustrating an exemplary ECG signal according to some embodiments of the present disclosure.

Merely by way of example, FIG. 10 illustrates an exemplary respiratory signal 1000, and FIG. 11 illustrates an exemplary ECG signal. FIG. 10 shows a respiratory signal 1000 extracted from the radar echo signal after the rigid motion correction. The respiratory signal may include a respiratory waveform. The respiratory waveform may include a plurality of respiratory cycles. FIG. 11 shows an ECG signal extracted from the radar echo data after the rigid motion correction. The ECG signal may be extracted based on the Q channel and I channel of the radar echo signal. Q channel and I channel are two orthogonal channels of the radar.

Figure 12:
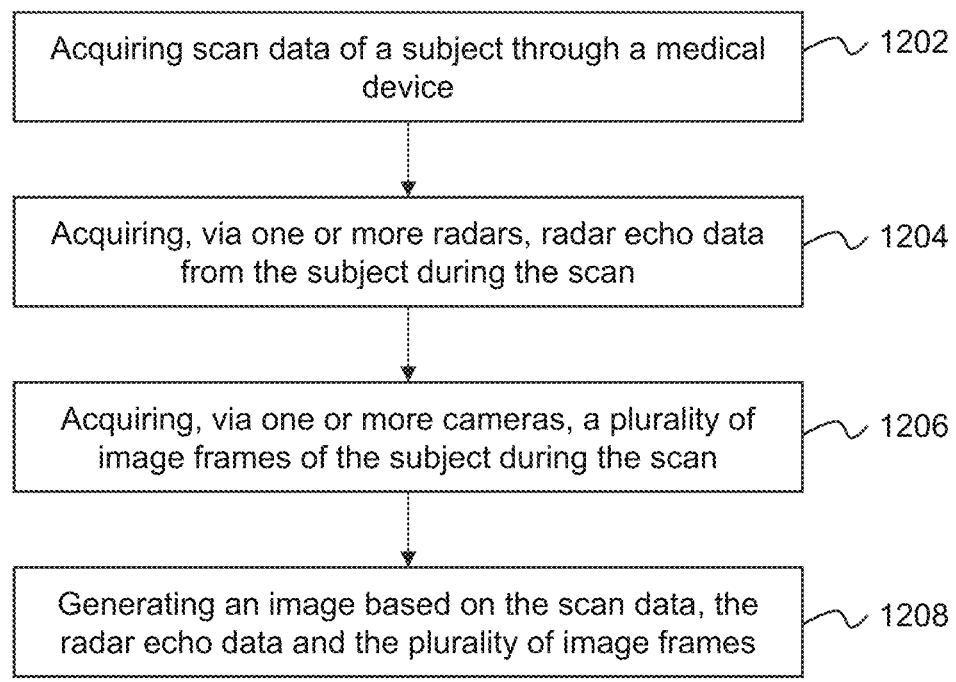
FIG. 12 is a flowchart illustrating an exemplary process for generating an image according to some embodiments of the present disclosure.

FIG. 12 is a flowchart illustrating an exemplary process for generating an image according to some embodiments of the present disclosure. Process 1200 may be implemented in the medical system 100 illustrated in FIG. 1 or the medical imaging system 500 illustrated in FIG. 5. For example, the process 1200 may be stored in the storage device 130 and/or the storage device 550 in the form of instructions (e.g., an application), and invoked and/or executed by the processing device 120 (e.g., the processing device 540 illustrated in FIG. 5, or one or more modules in the processing device 540 illustrated in FIG. 6). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1202, the processing device (e.g., the acquisition module 602 of the processing device 540) may acquire scan data of a subject through a medical device. For example, during the medical device (e.g., an MRI device) scans the subject or at least a part of the subject, the acquisition module 602 may acquire the scan data related to the subject or the at least a part of the subject in real time or near real time. The acquired scan data may be stored in a storage device (e.g., the storage device 550).

In 1204, the processing device (e.g., the acquisition module 602 of the processing device 540) may acquire, via one or more radars, radar echo data from the subject during the scan. The radar echo data may be used to characterize a physiological motion (i.e., the second motion mentioned above) of the subject. In some embodiments, the one or more radars may be installed at suitable positions on or in the vicinity of the medical device in order to capture radar echo signals indicative of the physiological motion of the subject. In some embodiments, the radar echo data may be stored in a storage device (e.g., the storage device 550).

In 1206, the processing device (e.g., the acquisition module 602 of the processing device 540) may acquire, via one or more cameras, a plurality of image frames of the subject. The radar echo data may be used to characterize a rigid motion (i.e., the first motion mentioned above) of the subject. In some embodiments, the one or more cameras may be installed at suitable positions on or in the vicinity of the medical device in order to capture the plurality of image frames for identifying the rigid motion of the subject. In some embodiments, the plurality of image frames may be stored in a storage device (e.g., the storage device 550).

In 1208, the processing device (e.g., the reconstruction module 610 of the processing device 540) may generate an image based on the scan data, the radar echo data and the plurality of image frames (operation 1008).

In some embodiments, the medical device may acquire the scan data continuously according to a retrospective gating technique. The reconstruction module 610 may obtain reconstruction data from the scan data based on the radar echo data and the plurality of image frames. However, in some embodiments, the one or more radars may detect both the physiological motion (i.e., the second motion) and the rigid motion (i.e., the first motion) if there exists the rigid motion during the scan. In this case, if the radar echo data without a correction is used to determine physiological motion related data directly, the determined physiological motion related data may be inaccurate because the radar echo data includes disturbed information caused by the rigid motion. To resolve this issue, the radar echo data may be corrected based on the plurality of image frames.

Specifically, the first data determination module 604 of the processing device 540 may determine, based on at least a part of the plurality of image frames, first data regarding the first motion (i.e., rigid motion related data). The first data may include one or more motion parameters of the rigid motion of the subject. The second data determination module 604 of the processing device 540 may correct the radar echo data according to the one or more motion parameters of the rigid motion. The second data determination module 604 may extract, from the corrected radar echo data, second data including cardiac motion data (e.g., the ECG signal illustrated in FIG. 11) and/or respiratory motion data (e.g., the ECG signal illustrated in FIG. 10). More detailed descriptions of first data and second data may be found elsewhere in the present disclosure, see, e.g., FIG. 8 and the descriptions thereof, and not repeated herein.

In some embodiments, the reconstruction module 610 may obtain the reconstruction data from the scan data based on the cardiac motion data or the respiratory data. For example, the reconstruction module 610 may obtain scan data corresponding to one or more specific cardiac cycles. The one or more specific cardiac cycles may be identified based on the cardiac motion data (e.g., the ECG signal). The scan data corresponding to the specific cardiac cycles may be designated as the reconstruction data. The reconstruction module 610 may reconstruct the image based on the designated reconstruction data. As another example, the reconstruction module 610 may obtain scan data corresponding to one or more specific respiratory cycles (e.g., one or more expiration periods). The one or more specific respiratory cycles may be identified based on the respiratory motion data (e.g., the respiratory signal). The scan data corresponding to the specific respiratory cycles may be designated as the reconstruction data. The reconstruction module 610 may reconstruct the image based on the designated reconstruction data. It should be understood that the fuse of the radar echo data and the image frames may be assisted to determine accurate cardiac motion data and respiratory motion data. The accurate cardiac motion data and respiratory motion data may facilitate to reduce or avoid motion artifacts (e.g., cardiac motion artifacts or respiratory motion artifacts) in the reconstructed image.

It should be noted that the description of the process 1200 is provided for the purposes of illustration, and not intended to limit the scope of the present disclosure. For persons having ordinary skills in the art, various variations and modifications may be conducted under the teaching of the present disclosure. For example, operations 1202 to 1206 may be integrated into a single operation, and/or be performed simultaneously. However, those variations and modifications may not depart from the protecting of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, radio frequency (RF), or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to surface modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for controlling a medical device, comprising:
obtaining, via one or more cameras, first data regarding a first motion of a subject in an examination space of the medical device, the first motion including a rigid motion of the subject;
obtaining, via one or more radars, radar echo data from the subject;
correcting the radar echo data based on the first data;
extracting, from the corrected radar echo data, second data regarding a second motion of the subject, the second motion including a physiological motion of the subject; and
generating, based on the first data and the second data, a control signal for controlling the medical device to scan at least a part of the subject.

2. The method of claim 1, further comprising:
obtaining scan data acquired by the medical device; and
reconstructing a medical image based on the scan data.

3. The method of claim 1, wherein the obtaining, via one or more cameras, first data regarding a first motion of a subject further includes:
acquiring, via the one or more cameras, a plurality of image frames regarding the first motion of the subject; and
determining, based on at least a part of the plurality of image frames, the first data including one or more motion parameters of the first motion.

4. The method of claim 3, wherein the one or more motion parameters of the first motion includes one or more translation matrices and one or more rotation matrices.

5. The method of claim 3, wherein
the second data includes cardiac motion data or respiratory motion data.

6. The method of claim 5, wherein the plurality of image frames and the radar echo data are acquired simultaneously by the one or more cameras and the one or more radars, respectively.

7. The method of claim 1, wherein the generating, based on the first data and the second data, a control signal for controlling the medical device to scan at least a part of the subject further includes:
generating, based at least in part on the second data, the control signal using a gating technique.

8. The method of claim 1, wherein the medical device includes at least one of a computed tomography (CT) device, a magnetic resonance imaging (MRI) device, a positron emission tomography (PET) device, or a radiation therapy (RT) device.

9. The method of claim 1, wherein the first data includes one or more motion parameters of the first motion in a camera coordinate system, and the correcting the radar echo data based on the first data includes:
transforming the one or more motion parameters of the first motion in the camera coordinate system into one or more motion parameters of the first motion in a radar coordinate system;
correcting the radar echo data based on the one or more motion parameters of the first motion in the radar coordinate system.

10. A system for controlling a medical device, comprising:
at least one storage device including a set of instructions; and
at least one processor in communication with the at least one storage device, wherein when executing the set of instructions, the at least one processor is directed to cause the system to:
obtain, via one or more cameras, first data regarding a first motion of a subject in an examination space of the medical device, the first motion includes a rigid motion of the subject;
obtain, via one or more radars, radar echo data from the subject;
correct the radar echo data based on the first data;
extract, from the corrected radar echo data, second data regarding a second motion of the subject, the second motion including a physiological motion of the subject; and
generate, based on the first data and the second data, a control signal for controlling the medical device to scan at least a part of the subject.

11. The system of claim 10, wherein the at least one processor is further directed to cause the system to:
obtain scan data acquired by the medical device; and
reconstruct a medical image based on the scan data.

12. The system of claim 10, wherein to obtain, via one or more cameras, first data regarding a first motion of a subject in an examination space of the medical device, the at least one processor is further directed to cause the system to:
acquire, via the one or more cameras, a plurality of image frames regarding the first motion of the subject; and
determine, based on at least a part of the plurality of image frames, the first data including one or more motion parameters of the first motion.

13. The system of claim 12, wherein the one or more motion parameters of the first motion includes one or more translation matrices and one or more rotation matrices.

14. The system of claim 12, wherein
the second data includes cardiac motion data or respiratory motion data.

15. The system of claim 14, wherein the plurality of image frames and the radar echo data are acquired simultaneously by the one or more cameras and the one or more radars, respectively.

16. The system of claim 10, wherein to generate, based on the first data and the second data, a control signal for controlling the medical device to scan at least a part of the subject, the at least one processor is further directed to cause the system to:
generate, based at least in part on the second data, the control signal using a gating technique.

17. The system of claim 10, wherein the medical device includes at least one of a computed tomography (CT) device, a magnetic resonance imaging (MRI) device, a positron emission tomography (PET) device, or a radiation therapy (RT) device.

18. The system of claim 10, wherein the first data includes one or more motion parameters of the first motion in a camera coordinate system, and to correct the radar echo data based on the first data, the at least one processor is further directed to cause the system to:
transform the one or more motion parameters of the first motion in the camera coordinate system into one or more motion parameters of the first motion in a radar coordinate system; and
correct the radar echo data based on the one or more motion parameters of the first motion in the radar coordinate system.

19. A medical system, comprising:
a medical device;
one or more cameras for acquiring a plurality of image frames of a subject in an examination space of the medical device;
one or more radars for acquiring radar echo data from the subject;
at least one storage device including a set of instructions; and
at least one processor in communication with the at least one storage device, wherein when executing the set of instructions, the at least one processor is directed to cause the medical system to:
determine, based on the plurality of image frames, first data regarding a first motion of the subject, the first motion including a rigid motion of the subject;
correct the radar echo data based on the first data;
extract, from the corrected radar echo data, second data regarding a second motion of the subject, the second motion including a physiological motion of the subject; and
generate, based on the first data and the second data, a control signal for controlling the medical device to scan at least a part of the subject.

20. The medical system of claim 19, wherein the at least one processor is directed to cause the medical system to:
obtain scan data acquired by the medical device; and
reconstruct a medical image based on the scan data.

* * * * *